(12) United States Patent
Chanduszko et al.

(10) Patent No.: US 11,285,027 B1
(45) Date of Patent: Mar. 29, 2022

(54) ENDOVASCULAR APPARATUS WITH ENHANCED RETRIEVABILITY AND RELATED METHODS

(71) Applicant: C.R. BARD, INC., Tempe, AZ (US)

(72) Inventors: Andrzej J. Chanduszko, Chandler, AZ (US); Michael Randall, Gilbert, AZ (US); William Parmentier, Tempe, AZ (US)

(73) Assignee: C.R. Bard, Inc., Tempe, AZ (US)

( * ) Notice: Subject to any disclaimer, the term of this patent is extended or adjusted under 35 U.S.C. 154(b) by 0 days.

(21) Appl. No.: 16/733,583

(22) Filed: Jan. 3, 2020

Related U.S. Application Data (60) Provisional application No. 62/787,985, filed on Jan. 3, 2019.

(51) Int. Cl.
| | | |
|---|---|---|
| *A61F 2/82* | (2013.01) | |
| *A61F 2/86* | (2013.01) | |
| *A61F 2/90* | (2013.01) | |
| *A61F 2/95* | (2013.01) | |

(52) U.S. Cl.
CPC .............. *A61F 2/90* (2013.01); *A61F 2/82* (2013.01); *A61F 2/86* (2013.01); *A61F 2/95* (2013.01); *A61F 2002/9528* (2013.01); *A61F 2210/0076* (2013.01); *A61F 2230/0041* (2013.01)

(58) Field of Classification Search
CPC ...... A61F 2/90; A61F 2/95; A61F 2/82; A61F 2/86; A61F 2002/9528; A61F 2210/0076; A61F 2230/0041
See application file for complete search history.

(56) References Cited

U.S. PATENT DOCUMENTS

| | | |
|---|---|---|
| 5,843,164 A | 12/1998 | Frantzen et al. |
| 6,464,665 B1 | 10/2002 | Heuser |
| 6,932,837 B2 | 8/2005 | Amplatz et al. |
| 6,989,021 B2 | 1/2006 | Bosma et al. |
| 7,338,512 B2 | 3/2008 | McGuckin, Jr. et al. |
| 7,582,100 B2 | 9/2009 | Johnson et al. |
| 7,854,757 B2 | 12/2010 | Fleming, III |
| 7,993,387 B2 | 8/2011 | Clere et al. |

(Continued)

FOREIGN PATENT DOCUMENTS

| | | |
|---|---|---|
| CN | 109700582 A | 5/2019 |
| JP | 2000262632 A | 9/2000 |
| JP | 201889108 A | 6/2018 |

OTHER PUBLICATIONS

English Machine Translation for CN109700582 dated May 3, 2019.

(Continued)

*Primary Examiner* — Dinah Baria
(74) *Attorney, Agent, or Firm* — Dickinson Wright PLLC; Andrew D. Dorisio (57) ABSTRACT

An endovascular apparatus takes the form of an expandable tubular body having a retriever, which may include a pair of interconnected hooks. The retriever may be formed from a single piece of material forming the tubular body, and in the case of a pair of hooks thus has a thickness corresponding to approximately twice the wall thickness of the tubular body. The innermost radial portion of the hooks may be offset from a central axis of a lumen formed by the tubular body, which facilitates free insertion of a balloon or the like for purposes of expanding the tubular body. Related methods of manufacturing an endovascular apparatus with a retriever are also described herein.

20 Claims, 8 Drawing Sheets

(56) References Cited

U.S. PATENT DOCUMENTS

| | | |
|---|---|---|
| 8,795,318 B2 | 8/2014 | Hallisey et al. |
| 9,011,479 B2 | 4/2015 | Koehler |
| 9,056,024 B2 | 6/2015 | Tippett et al. |
| 9,579,427 B2 | 2/2017 | Choubey et al. |
| 2009/0105747 A1 | 4/2009 | Chanduszko et al. |
| 2009/0234429 A1 | 9/2009 | Lau |
| 2009/0299404 A1 | 12/2009 | Chanduszko et al. |
| 2010/0010622 A1 | 1/2010 | Lowe et al. |
| 2011/0071613 A1 | 3/2011 | Wood et al. |
| 2013/0226067 A1 | 8/2013 | Ward et al. |
| 2016/0089255 A1 | 3/2016 | Bergheim et al. |
| 2017/0000939 A1 | 1/2017 | Cully et al. |

OTHER PUBLICATIONS

English Machine Translation for JP2000262632A dated Sep. 26, 2000.

English Machine Translation for JP201889108A dated Jun. 14, 2018.

ENDOVASCULAR APPARATUS WITH ENHANCED RETRIEVABILITY AND RELATED METHODS

This application claims the benefit of U.S. Provisional Patent Application No. 62/787,985, filed on Jan. 3, 2019, the disclosure of which is incorporated herein by reference.

TECHNICAL FIELD

This disclosure pertains to medical apparatuses and, in particular, to an endovascular apparatus with enhanced retrievability and related methods.

BACKGROUND

As is well known, a variety of medical apparatuses are adapted for use in endovascular installation and use, such as for example a vascular stent, filter, plug, or the like. A typical vascular stent is a flexible, elongated, tubular structure made of a biocompatible material, designed for expansion in a vessel. Once expanded, the stent thus forms a support scaffold to assist in maintaining patency of the corresponding vessel.

To facilitate endovascular placement, a significant amount of focus has been directed toward making such apparatus as thin and generally small/compressed profile as possible. While significant advances in technology have been made in this regard, past proposals for have suffered from certain limitations. For instance, from time-to-time, it may be necessary or desirable to remove or reposition an endovascular apparatus after initial placement. Although theoretically this simply requires moving the apparatus within the vessel, the above-mentioned efforts to make the endovascular apparatus extraordinarily thin and flexible to facilitate insertion have compromised the ability to retrieve/recover and move/remove the apparatus, at least without complexity and the potential for complications.

Stent design may also impact the flow dynamics in stented segments of vessel. In particular, the thickness of the struts forming the stent plays a major role in local shear rate and endothelial shear stress post-percutaneous intervention. Large strut thickness increases the amount of foreign material in the lumen and can lead to flow disturbances, flow separation, and areas of recirculation zones. Consequently, the risk of deleterious stent thrombosis is increased by efforts to make the stent more robust by simply increasing strut thickness or providing a retriever that may create significant flow obstructions.

Accordingly, it would be desirable to provide an endovascular apparatus, including but not limited to a stent, filter, or plug, that is sufficiently robust to allow for ready retrieval without undue complexity or complication, and which seeks to minimize any contribution to the above-described deleterious phenomenon associated with percutaneous intervention.

SUMMARY

An object of the invention is to provide an endovascular apparatus, such as a vascular stent, filter, plug, or the like, with enhanced retrievability and also methods for making such an endovascular apparatus.

With that objective in mind, and according to a first aspect of the disclosure, an endovascular apparatus, such as for example, a stent, a filter, or a plug, is adapted for retrieval using a snare. The apparatus comprises a body having a wall forming a lumen, the wall comprising a material having a thickness, and further having a pair of hooks, each hook of the pair of hooks having a first longitudinal portion extending from and unitarily formed with the wall and a second portion connected to the longitudinal portion. The longitudinal portions may be bent or twisted, such that the second portions of the interconnected hooks together form a receiver adapted to receive the snare. Each hook is formed of the material of the wall having the thickness.

In some embodiments, the pair of hooks are at least partially connected together by a bond. The bond may comprise, for example, a weld. In some embodiments, the pair of interconnected hooks include a radially innermost portion offset from a central axis of the body. In this or other embodiments, the first longitudinal portion of each hook is partially twisted and the second portion projects radially inward from the first elongated portion. In this or other embodiments, the body includes an elongated spine connected to the pair of interconnected hooks as a single unitary structure.

In accordance with another aspect of the disclosure, an endovascular apparatus comprises a body having a wall forming a lumen and a hook having a radially innermost portion offset from a central axis of the lumen. In some embodiments, the hook comprises a pair of hook portions formed of a single thickness of the wall and connected together by a bond. In these or other embodiments, the body includes an elongated spine connected to the hook.

Still another aspect of the disclosure pertains to an endovascular apparatus comprising a body having a wall with a thickness and forming a lumen. The body includes a retriever formed of a double wall thickness of a single piece of material forming the body. In some embodiments, the retriever comprises a pair of J-shaped hooks bonded together and having an open end facing in a distal direction. In this or other embodiments, the retriever is offset from a central axis of the body. In some embodiments, the body comprises a spine connected to the retriever to form a single unitary structure.

This disclosure also relates to a method of forming an endovascular apparatus. The method comprises forming adjacent hooks in a tubular piece of material, each hook extending longitudinally and having a thickness the same as a wall of the tubular piece of material. The method further comprises bending the adjacent hooks.

In some embodiments, the method further includes the step of fastening the adjacent hooks to form a single hook assembly having a thickness equal to or greater than twice the thickness of the single piece of material. Still further, the fastening step may comprise welding the adjacent hooks. The bending step may comprise rotating the hooks inwardly and upwardly. The method may further comprise forming a mesh in the tubular piece of material. The forming step may comprise forming a spine connected to the adjacent hooks.

BRIEF DESCRIPTION OF THE DRAWING FIGURES

The above and further advantages according to the inventions disclosed herein may be better understood by referring to the following description in conjunction with the accompanying drawings in which.

The drawings are not necessarily drawn proportionally or to scale. For example, the dimensions of some of the elements may be exaggerated relative to other elements for clarity or several physical components may be included in one functional block or element. Further, sometimes reference numerals may be repeated among the drawings to indicate corresponding or analogous elements.

DETAILED DESCRIPTION

In the following detailed description, numerous specific details are set forth to provide a thorough understanding of the disclosed concepts. Those of ordinary skill in the art will know that the disclosed inventions may be practiced without these specific details. In other instances, well-known methods, procedures, components, or structures may not have been described in detail so as not to obscure the disclosed inventions.

The description provided below and in regard to the figures applies to all embodiments unless noted otherwise, and features common to each embodiment are similarly shown and numbered.

Figure 1:
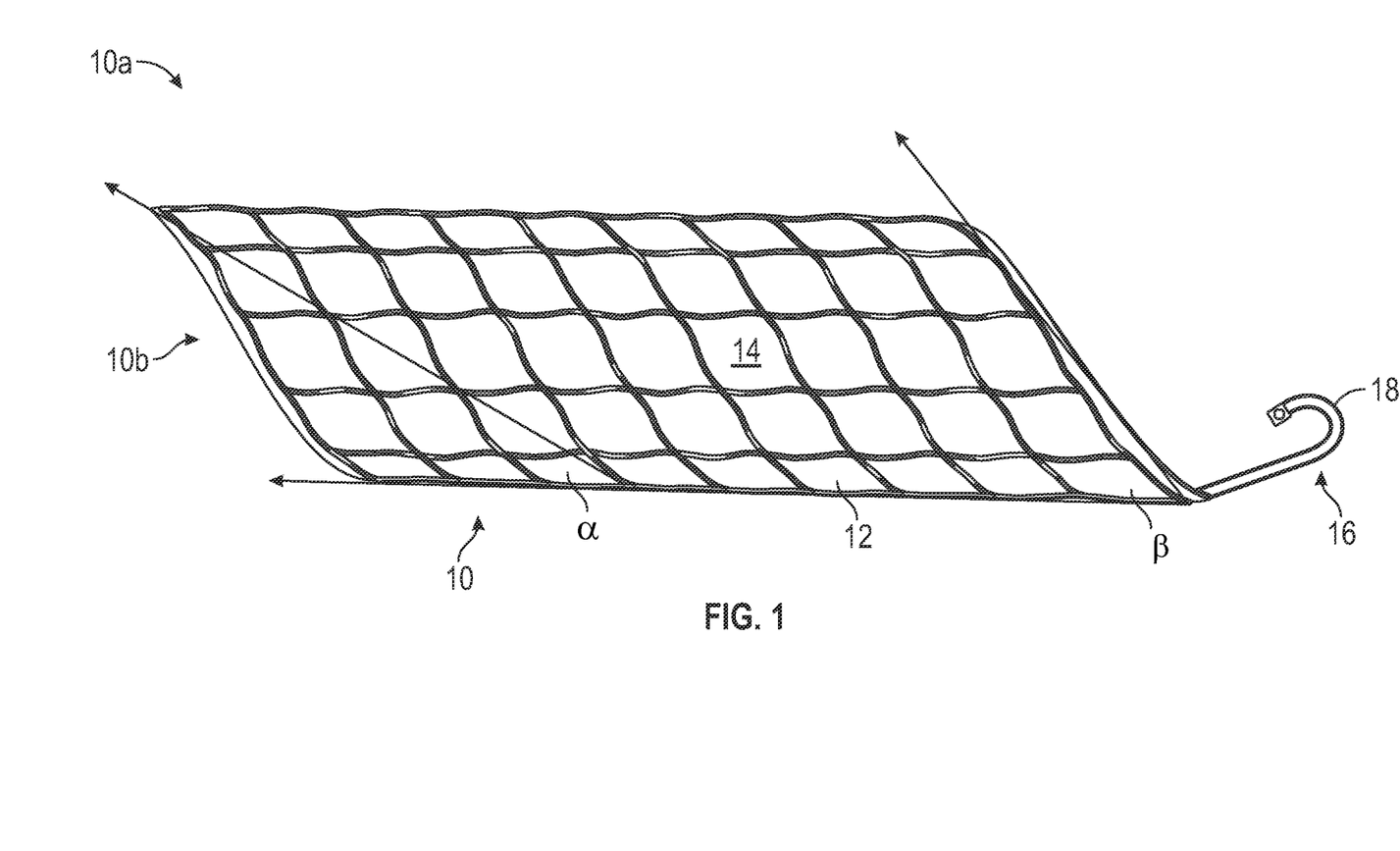
FIG. 1 is an elevational side view of one embodiment of an endovascular apparatus according to the disclosure.
Figure 2:
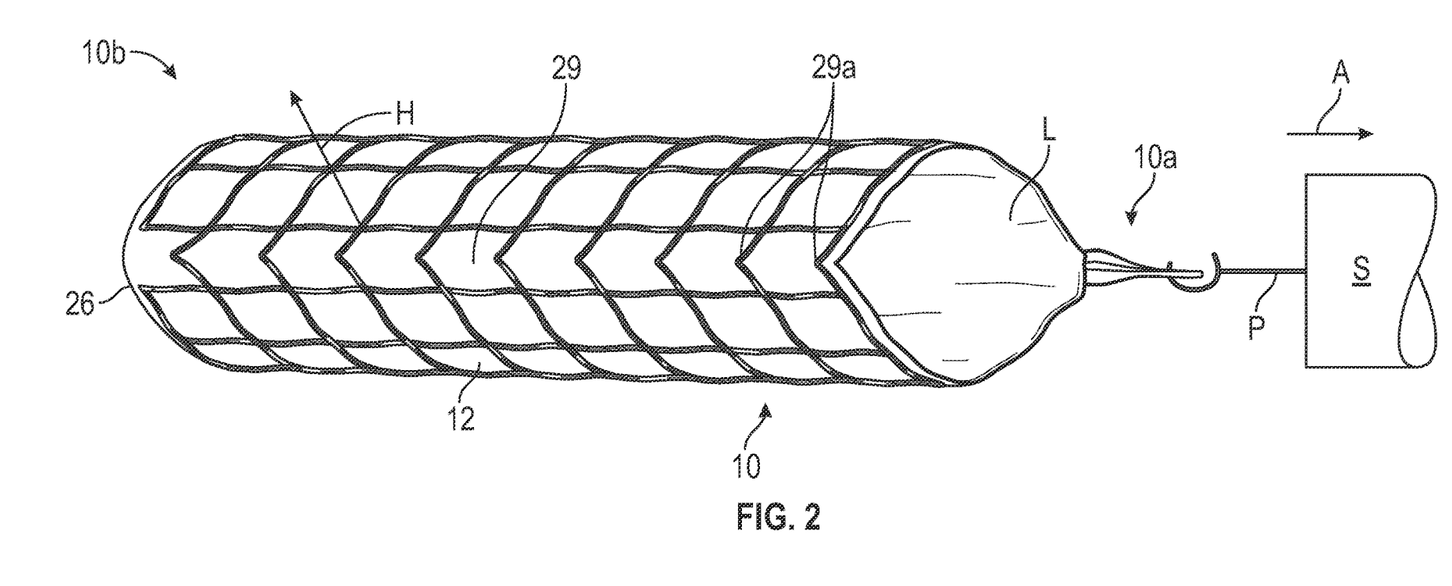
FIG. 2 is a top plan view of the apparatus of FIG. 1.
Figure 3:
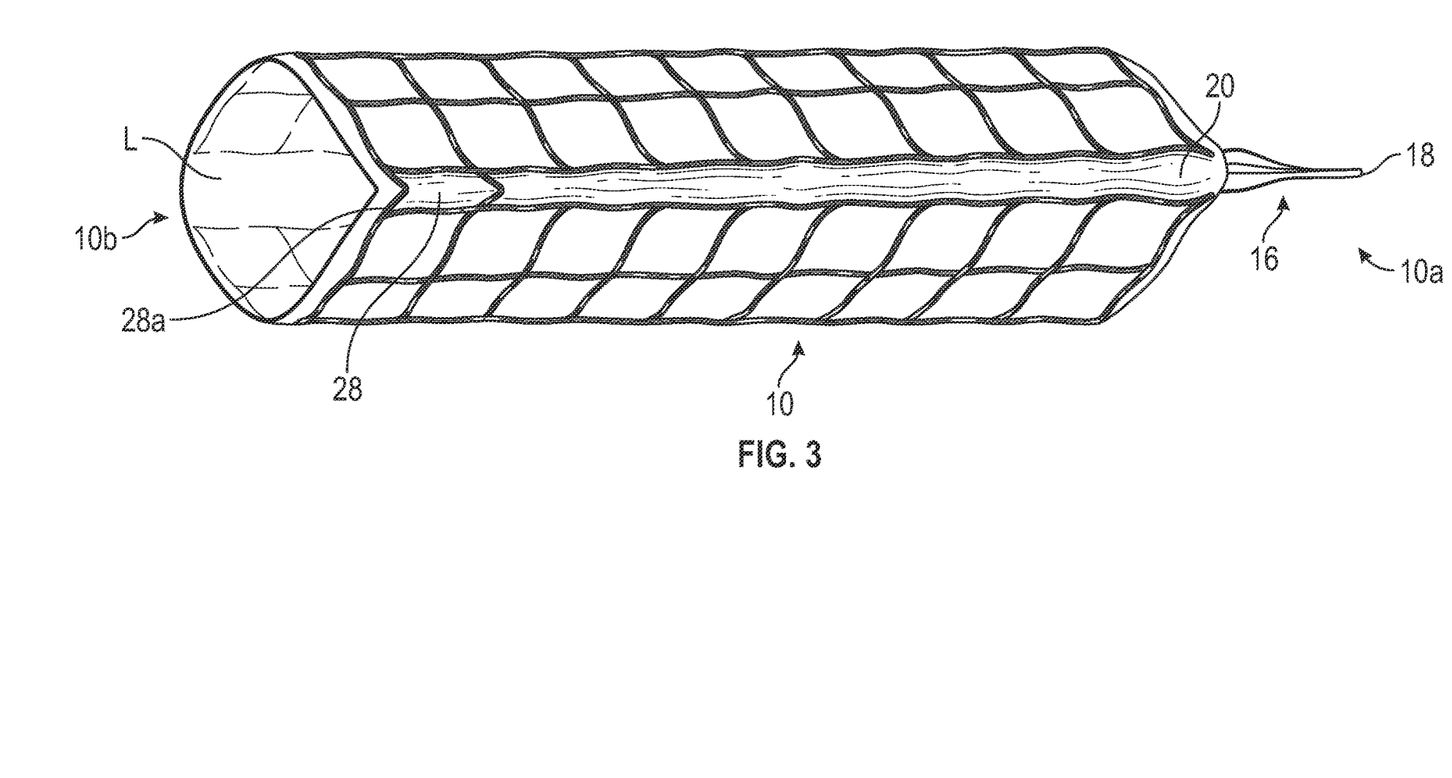
FIG. 3 is a bottom plan view of the apparatus of FIG. 2.

Referring first to FIGS. 1-3, an endovascular apparatus is shown in the form of a stent 10 for endovascular placement. As illustrated, the stent 10 comprises a body 12, which as illustrated may comprise a mesh formed of a plurality of closed cells 14 surrounding a lumen L for passing a flow of fluid, such as blood, in an associated vessel once inserted therein, while also lending support for the corresponding wall of the vessel to maintain patency.

The cells 14 of the body 12 forming stent 10 may have various shapes and sizes. Those shown have tapered ends and a wider central portion, and thus have the shape of a lemon in a top-down or plan view. As illustrated, the cells 14 may be oriented such that a direction of elongation is biased (that is, it extends at an angle $\alpha$ of approximately 30 degrees relative to a horizontal axis in a nominal orientation of the stent, as shown in FIG. 1). This orientation plus the shape of the cells 14 facilitates collapsing along a helical axis (see arrow H in FIG. 2), generally in the direction of compression, when the opposite side of the stent 10 is engaged by an external structure (such as a sheath).

As perhaps best understood from viewing FIGS. 1-3 together, a first end of the stent 10 may include a retriever 16, which in one embodiment takes the form of a hook 18, the details of which are outlined further in the following description. The hook 18 may be connected to and unitarily formed with an elongated spine 20 extending longitudinally along one side (e.g., an underside) of the stent 10 in the illustrated orientation, and is bounded on both lateral sides by the closed cells 14. This spine 20 is formed of material that is generally wider circumferentially than the wires or struts forming the closed cells, and thus enhances the ability of the stent 10 to be retrieved using the associated retriever 16 (hook 18). While only one spine 20 is shown, more than one may be present, if desired.

Figure 4:
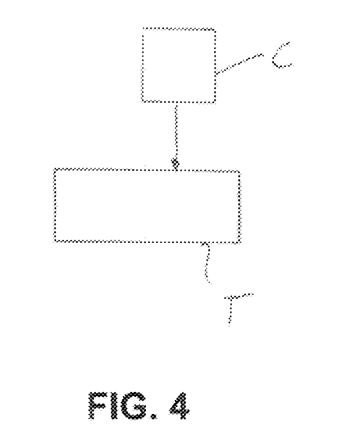
FIGS. 4 and 5 illustrate the manner in which the retriever may be formed from a single tubular piece of material.

It can also be understood that at least the end 10*a* associated with the retriever 16 may be sloped or tapered so as to form a second angle $\beta$ with a horizontal axis. As can be appreciated, when the retriever 16 is pulled longitudinally for purposes of retrieving the stent 10, this taper allows for the narrower tapered portion of the stent to initially enter a sheath S when pulled by a snare P toward the opening thereof in the direction of arrow A (see FIG. 2). Further longitudinal movement of the stent 10 into the sheath S may thus cause a partial collapse to ensure recovery, even if the inner diameter of the sheath S is much smaller than the outer diameter of the stent 10 (e.g., the sheath diameter would typically be similar to the radial extent of the hook 18). The opposite or distal end (relative to the retriever 16) may also be similarly tapered, as shown, but could also be vertically oriented (as indicated in FIG. 4).

With reference to FIG. 2, the upper portion of the stent 10 in the orientation shown (which may or may not be representative of the orientation in use, depending on the application) may have closed cells 24. The associated transverse struts or wires 24*a* forming part of the mesh of the body 12 may be generally V-shaped in a top-down or plan view. As can be appreciated, this arrangement creates a hinge that facilitates the collapsing or folding of the stent along the corresponding axis when the retriever 16 is pulled and the periphery of the corresponding end 10*a* is engaged, such as by the periphery of a sheath S. The last cell 26 in the series, associated with a longitudinal apex at the opposite end 10*b* of the stent 10 may be open, and thus may simply collapse without relying on a hinge.

Referring now to FIG. 3, an optional closed cell 28 may also be provided along the end 10*a* of the stent 10 associated with the spine 20, but generally opposite the retriever 16 (hook 18). A leading end of this cell 28 may be associated with a generally transverse wire 28*a* that is also V-shaped so as to form a hinge. This hinge, combined with the open cell 26 at the opposite side, facilitates the controlled collapsing or folding of the corresponding end 10*a* of the stent 10.

Figure 5:
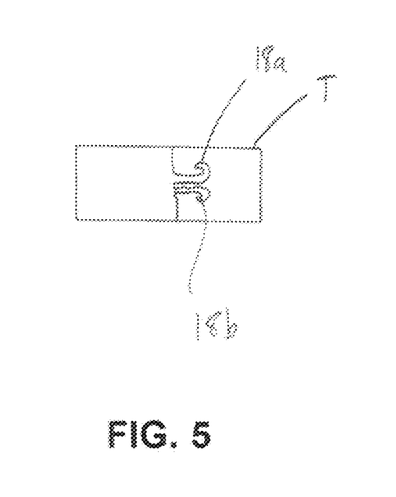

Formation of the stent 10 (or other endovascular apparatus) may be achieved by cutting the tubular body 12 from a single piece of tubular material. Specifically, as shown in FIGS. 4 and 5, an elongated tube T of material may be initially solid-walled, and cut using a cutter C, such as for example a laser cutter. This processing allows for two longitudinally extending hooks 18*a*, 18*b* to be cut directly from the single thickness material forming the wall of the tube T, which may be considered to create a preform for forming an endovascular apparatus. The hooks 18*a*, 18*b* may be folded or bent (as discussed below in further detail) into a juxtaposed, abutting relationship, and then bonded together to form a double thickness hook 18 serving as the retriever 16 of FIG. 1. Either prior to or after the formation of the double hook 18, the tube T may be further modified (cut) to form the desired endovascular apparatus. It can be appreciated that, in view of the cutting process described above, the nominal diameter of the tube T corresponds with the diameter of the resulting endovascular apparatus, and the height of the hooks 18*a*, 18*b* (proportional to the amount of cutting in the circumferential direction) may be substantially smaller in relation to this diameter (see, e.g., FIGS. 7-8 below).

Figure 6:
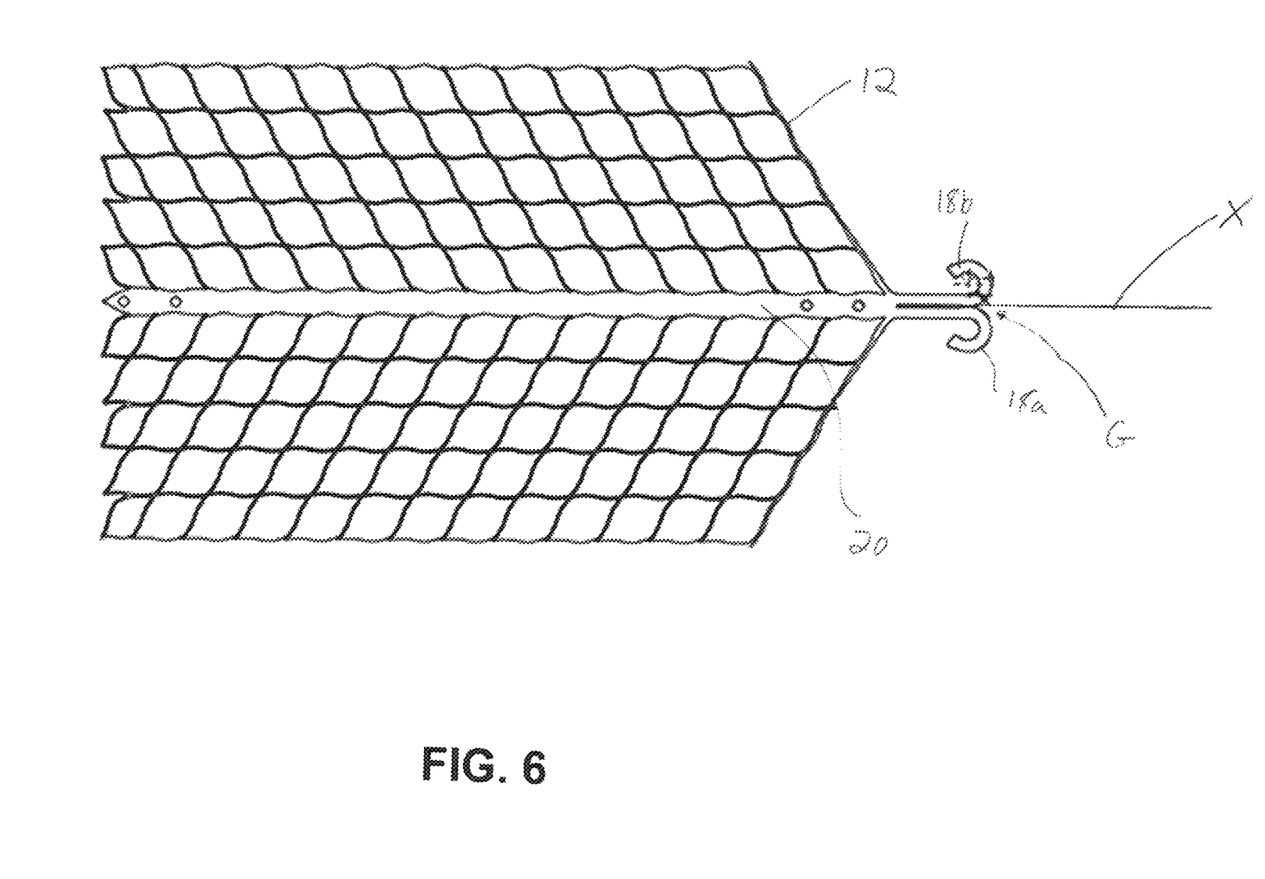
FIG. 6 is a flat pattern view of an alternate embodiment of the apparatus.

If the tubular body 12 were cut longitudinally and laid flat, as shown in the bottom plan view of FIG. 6, it can be understood that hooks 18*a*, 18*b* may be cut at the proximal end of the spine 20, if present. The hooks 18*a*, 18*b* may be generally symmetrical about a longitudinal axis C of the spine 20, with each hook formed of a single thickness of the material of the tubular body. However, inclusion of the spine 20 is considered optional in all disclosed embodiments.

Figure 7:
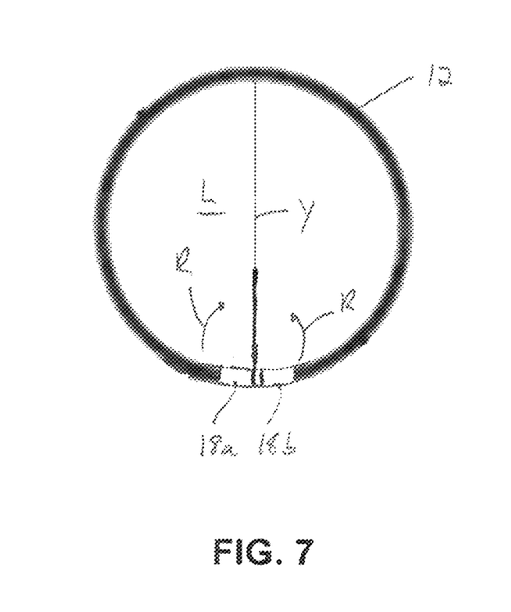
FIGS. 7 and 8 are schematic views of manufacturing steps that may be used to form the apparatus.
Figure 8:
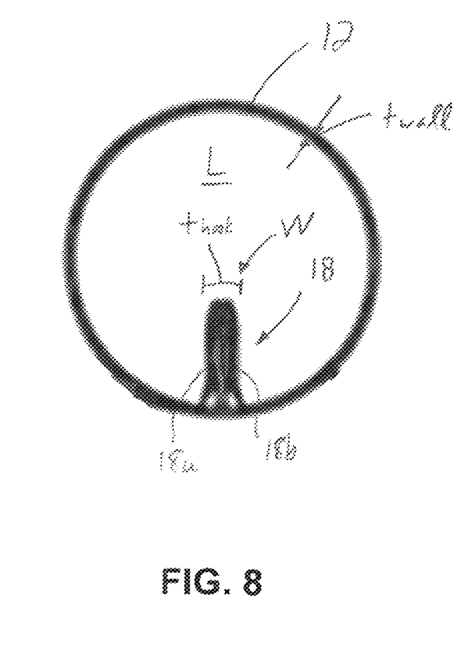

Turning now to FIGS. 7 and 8, one particular manner by which the two single thickness hooks 18a, 18b may be configured to form a single hook 18 to serve as the retriever for an endovascular apparatus is illustrated. As shown in FIG. 7, the independent hooks 18a, 18b initially extend longitudinally in-line with the associated body 12 once cut from the single tube, and are considered to be generally J-shaped (each thus having an elongated portion extending from the wall of the tubular body 12 in a longitudinal direction and a curved portion connected to the elongated portion and having an open end having a receiver for receiving a snare, but the hooks being separated from each other by a small gap G). The hooks 18a, 18b may then be bent by being rotated upwardly and inwardly toward a central vertical axis Y of the tubular body 12 until the orientation shown in FIG. 1 is achieved, with the inner faces of the hooks being in an opposing and partially abutting relationship. The elongated portions of the hooks 18a, 18b thus become twisted as a result of this bending and folding action. The hooks 18a, 18b may then be fastened together, such as by welding using a permanent adhesive or weld W, so as to form the single hook 18 comprised of a double thickness of the wall material of the body 12 ($t_{hook} \geq 2$ times $t_{wall}$). Also, the single hook 18 extends radially, and has a corresponding radial dimension that is less than or equal to the radius of the associated body 12.

As a result of this arrangement, a strong, unitary retriever 16 is thus formed, which may be connected to the spine 20 if present, to thus allow for robust pulling or repositioning of the stent 10 or other associated endovascular apparatus for purposes of retrieval. From FIG. 8, it can also be understood that the double thickness hook 18 is a low-profile structure relative to the area of the lumen L, extending radially inwardly from only one side and thus having a radially innermost portion offset from a central longitudinal axis of the lumen L, and otherwise arranged so that the creation of turbulence is minimized. The hook 18 tends not to interfere with flow therethrough and, therefore, helps to avoid contributing to thrombosis in the case of blood flow and other deleterious conditions associated with endovascular procedures. In the case of an endovascular apparatus expanded with a balloon after placement (such as a stent), this low-profile hook 18 also makes it easier to deliver a guidewire and balloon through the lumen L without interference.

As can be appreciated from FIGS. 1 and 4, the formation of the hooks 18a, 18b in the proposed manner (cut from the wall of a single tube) also allows for the creation of an oversized, distal-facing opening in the resulting single hook 18. Despite the low-profile, this significantly enhances the ability to retrieve the associated apparatus, such as stent 10, via a snare, which can simply be drawn proximally into engagement with the interior of the hook 18 via the open end (which interior may comprise from about 180° to about 270° of the curved portion of the hook). This is considered far easier to achieve then past arrangements where a retriever is formed by simply cutting a slot into a small diameter tube of which the associated stent is simply an expanded portion thereof (see, e.g., U.S. Pat. No. 6,989,021, the disclosure of which is incorporated herein by reference). The combined nature of the hooks 18a, 18b into the single hook 18 also helps to ensure that both hooks will be captured together with a snare, whereas, in past arrangements with spaced hooks, if only one hook is captured, it would be nearly impossible to retrieve the apparatus.

Figure 9:
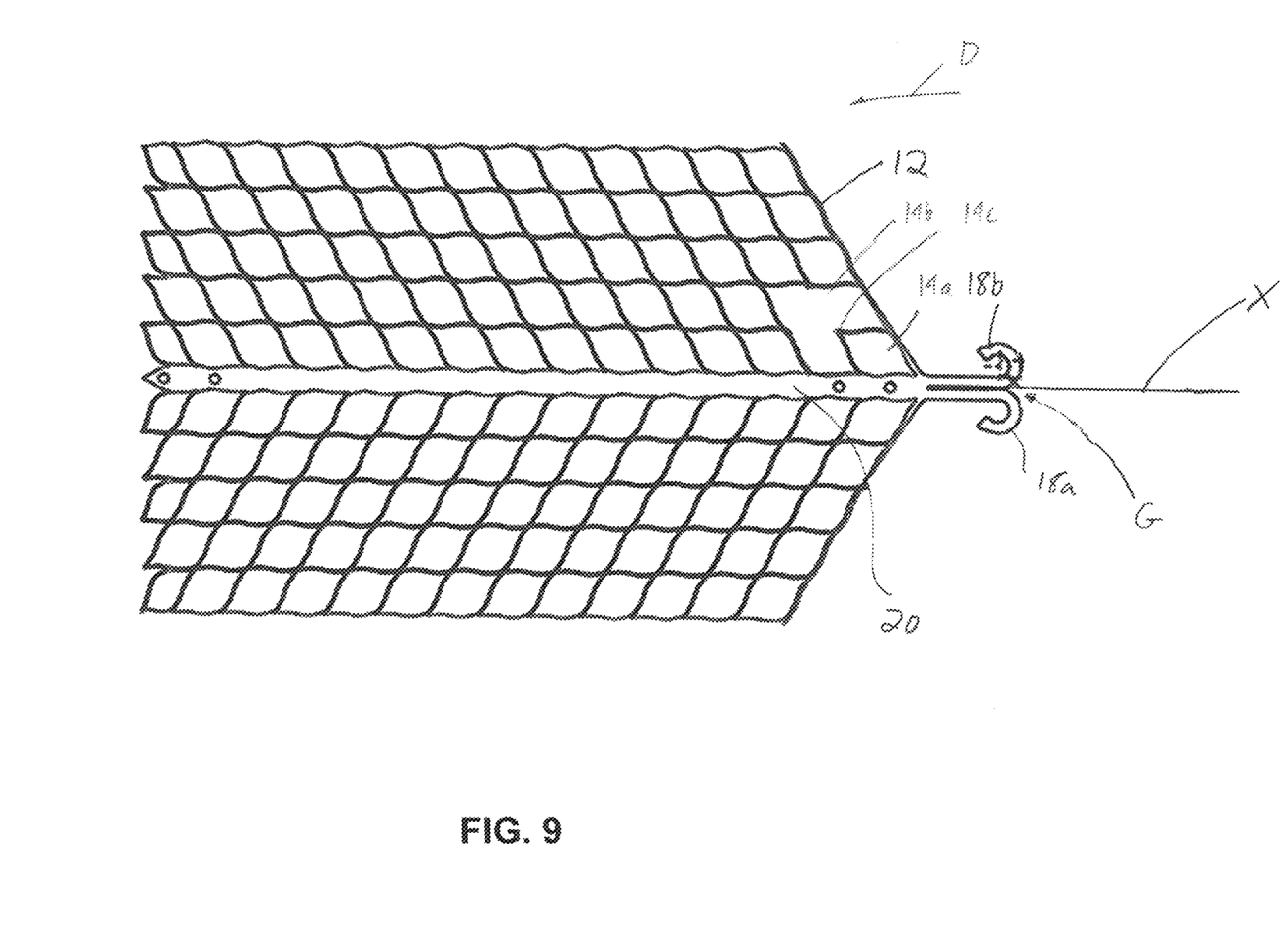
FIG. 9 is a flat pattern view of another alternate embodiment of the apparatus.

With reference to FIG. 9, it can be appreciated that certain of the cells 14 may be different sizes or shapes. For example, a smaller cell 14a may have an apex 14c that is within a larger cell 14b, and not connected to it. In such case, the apex 14c extends in a direction D away from the retriever 16 (hook) such that it is caused to collapse when pulled into the sheath and does not get snagged as a result. As can be appreciated, this arrangement may be repeated as necessary or desired, and may be applied to any disclosed embodiment.

Figure 10:
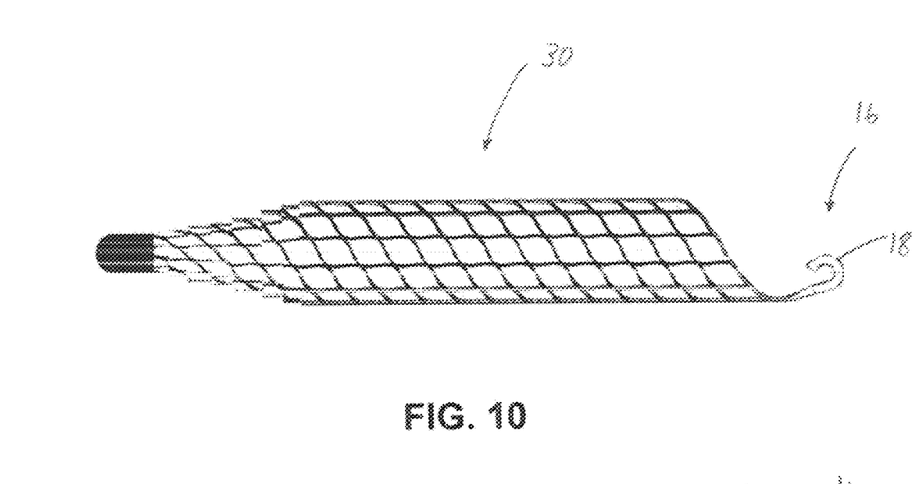
FIGS. 10 and 11 are side views of alternative forms of endovascular apparatuses that may benefit from the teachings herein.
Figure 11:
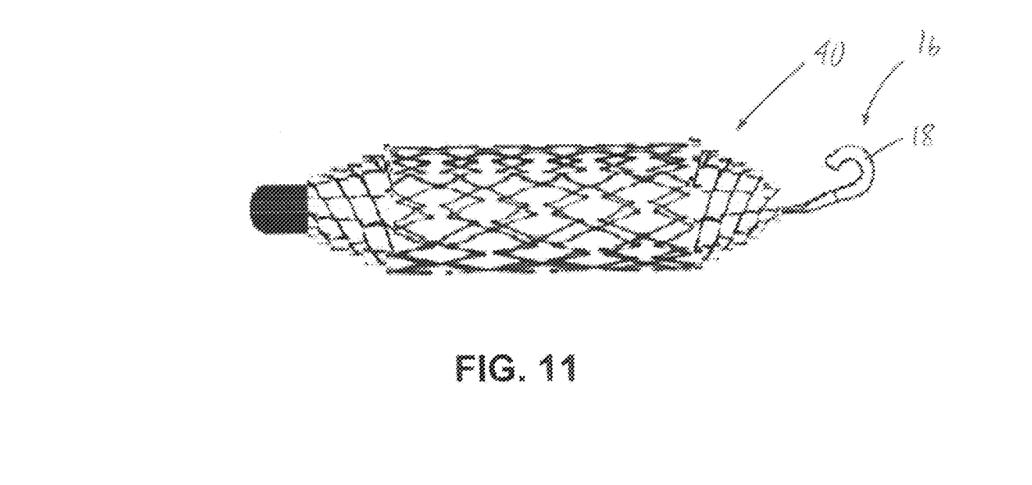

As previously indicated, the application of this retriever formed by the hook 18 is not limited to stents, but can be applied to any endovascular apparatus in need of retrieval. For instance, as shown in FIG. 10, an embolic filtration apparatus 30 may benefit from the technology described herein, including the retriever 16 in the form of a hook 18 and/or the associated spine (not shown). Likewise, as shown in FIG. 11, an endovascular plug 40 may also benefit from the use of the retriever 16 in the form of a hook 18 and/or spine (not shown) to enhance retrievability or repositioning.

Turning back to FIGS. 1-3, it can also be understood that the stent 10 or any other endovascular apparatus used may be provided with a material along the luminal surface to promote the smooth and regular flow of fluid. The material may comprise, for example expanded polytetrafluoroethylene ("ePTFE"), but other materials may be used. The use of such material may also help to prevent incorporation of the stent 10 or other endovascular apparatus into the tissue, and thus promote retrieval.

The endovascular apparatus may be made of a variety of materials. For example, the apparatus may be fabricated from a shape memory material, such as Nitinol, or other metals/alloys, such as stainless steel, nickel-chromium, titanium alloys, or the like. The stent material may also be formed of a polymer material, or even a bioabsorbable material, such as magnesium or other such materials. The stent 10 may also be coated with a medicine or pharmacological agent for treatment purposes, as is known in the art.

Each of the following terms written in singular grammatical form: "a", "an", and "the", as used herein, means "at least one", or "one or more". Use of the phrase "one or more" herein does not alter this intended meaning of "a", "an", or "the". Accordingly, the terms "a", "an", and "the", as used herein, may also refer to, and encompass, a plurality of the stated entity or object, unless otherwise specifically defined or stated herein, or, unless the context clearly dictates otherwise. For example, the phrases: "a unit", "an apparatus", "an assembly", "a mechanism", "a component, "an element", and "a step or procedure", as used herein, may also refer to, and encompass, a plurality of units, a plurality of apparatuses, a plurality of assemblies, a plurality of mechanisms, a plurality of components, a plurality of elements, and, a plurality of steps or procedures, respectively.

Each of the following terms: "includes", "including", "has", "having", "comprises", and "comprising", and, their linguistic/grammatical variants, derivatives, or/and conjugates, as used herein, means "including, but not limited to", and is to be taken as specifying the stated component(s), feature(s), characteristic(s), parameter(s), integer(s), or step(s), and does not preclude addition of one or more additional component(s), feature(s), characteristic(s), parameter(s), integer(s), step(s), or groups thereof. Each of these terms is considered equivalent in meaning to the phrase "consisting essentially of." Each of the phrases "consisting of and "consists of, as used herein, means "including and limited to". The phrase "consisting essentially of" means that the stated entity or item (system, system unit, system sub-unit apparatus, assembly, sub-assembly, mechanism, structure, component element or, peripheral equipment utility, accessory, or material, method or process, step or procedure, sub-step or sub-procedure), which is an entirety or part of an exemplary embodiment of the disclosed invention, or/and which is used for implementing an exemplary embodiment of the disclosed invention, may include at least one additional feature or characteristic" being a system unit system subunit apparatus, assembly, sub-assembly, mechanism, structure, component or element or, peripheral equipment utility, accessory, or material, step or procedure, sub-step or sub-procedure), but only if each such additional feature or characteristic" does not materially alter the basic novel and inventive characteristics or special technical features, of the claimed item.

The term "method", as used herein, refers to steps, procedures, manners, means, or/and techniques, for accomplishing a given task including, but not limited to, those steps, procedures, manners, means, or/and techniques, either known to, or readily developed from known steps, procedures, manners, means, or/and techniques, by practitioners in the relevant field(s) of the disclosed invention.

Terms of approximation, such as the terms about, substantially, approximately, etc., as used herein, refers to ±10% of the stated value. Use of the terms parallel or perpendicular are meant to mean approximately meeting this condition, unless otherwise specified.

It is to be fully understood that certain aspects, characteristics, and features, of the invention, which are, for clarity, illustratively described and presented in the context or format of a plurality of separate embodiments, may also be illustratively described and presented in any suitable combination or sub-combination in the context or format of a single embodiment. Conversely, various aspects, characteristics, and features, of the invention which are illustratively described and presented in combination or sub-combination in the context or format of a single embodiment may also be illustratively described and presented in the context or format of a plurality of separate embodiments.

Although the inventions of this disclosure have been illustratively described and presented by way of specific exemplary embodiments, and examples thereof, it is evident that many alternatives, modifications, or/and variations, thereof, will be apparent to those skilled in the art. For example, while a pair of hooks is described above, it can be appreciated that more than two hooks can be used to form the single hook. Likewise, multiple single hooks, each formed of a double hook, can be provided on a single device, if desired for a particular use. Accordingly, it is intended that all such alternatives, modifications, or/and variations, fall within the spirit of, and are encompassed by, the broad scope of the appended claims.

The invention claimed is:

1. An endovascular apparatus adapted for retrieval using a snare, comprising:
   a body having a wall forming a lumen, the wall comprising a material having a thickness, and further having a pair of interconnected hooks, each hook of the pair of interconnected hooks having a first longitudinal portion extending from and unitarily formed with the wall and a second portion connected to the first longitudinal portion, the second portions of the interconnected hooks together forming a receiver adapted to receive the snare, each hook being formed of the material of the wall having the thickness, the pair of interconnected hooks being bonded together by a bond between the first longitudinal portions or the second portions so as to form a single bonded hook having a double thickness of the wall material.

2. The endovascular apparatus of claim 1, wherein first longitudinal portions of the pair of hooks are at least partially connected together in a side-by-side fashion by the bond.

3. The endovascular apparatus of claim 2, wherein the bond comprises a weld fastening the pair of hooks together so as to form a single welded hook having a double thickness of the wall material.

4. The endovascular apparatus of claim 1, wherein the pair of interconnected hooks radially project into a longitudinal path of the lumen and include a radially innermost portion offset from a central axis of the body.

5. The endovascular apparatus of claim 1, wherein the first longitudinal portion of each hook is partially twisted and the second portion projects radially inward from the first elongated portion.

6. The endovascular apparatus of claim 1, wherein the body includes an elongated spine connected to the pair of interconnected hooks as a single unitary structure.

7. The endovascular apparatus of claim 6, wherein the body comprises stent including a plurality of struts, the spine being wider in a circumferential direction than each of the plurality of struts.

8. The endovascular apparatus of claim 1, selected from the group comprising a filter and a plug.

9. The endovascular apparatus of claim 1, wherein the body includes an end that is sloped or tapered so as to form an angle with a horizontal axis.

10. The endovascular apparatus of claim 1, wherein each hook is J-shaped.

11. An endovascular apparatus, comprising:
    a body having a wall forming a lumen and a pair of interconnected hooks radially projecting into a longitudinal path of the lumen and having a radially innermost portion offset from a central axis of the lumen, each hook of the pair of interconnected hooks having a first longitudinal portion extending from and unitarily formed with the wall and a second portion connected to the first longitudinal portion, the second portions of the interconnected hooks together forming a receiver, each hook being formed of the material of the wall having the thickness, the pair of interconnected hooks being bonded together by a bond between the first longitudinal portions or the second portions so as to form a single bonded hook having a double thickness of the wall material.

12. The endovascular apparatus of claim 11, wherein the body includes an elongated spine connected to the pair of interconnected hooks.

13. The endovascular apparatus of claim 11, wherein the hook is J-shaped.

14. An endovascular apparatus, comprising:
    a body comprising a wall with a thickness and forming a lumen, the body having a retriever formed of a pair of interconnected hooks, each hook of the pair of interconnected hooks having a first longitudinal portion extending from and unitarily formed with the wall and a second portion connected to the first longitudinal portion, the second portions of the interconnected hooks together forming a receiver, each hook being formed of the material of the wall having the thickness, the pair of interconnected hooks being bonded together by a bond between the first longitudinal portions or the second portions so as to form a single bonded hook having a double thickness of the wall material.

15. The endovascular apparatus of claim 14, wherein the retriever comprises a pair of J-shaped hooks bonded together and having an open end facing in a distal direction.

16. The endovascular apparatus of claim 14, wherein the retriever is offset from a central axis of the body.

17. The endovascular apparatus of claim 14, wherein the body comprises a spine connected to the retriever to form a single unitary structure.

18. The endovascular apparatus of claim 14, wherein the first and second portions of the wall in contact with each other are joined together by a weld.

19. The endovascular apparatus of claim 14, wherein the body comprises a single piece of tubular material.

20. An endovascular apparatus adapted for retrieval using a snare, comprising:

a body having a wall forming a lumen, the wall comprising a material having a thickness, and further having a pair of interconnected hooks, each hook of the pair of interconnected hooks having a first longitudinal portion extending from and unitarily formed with the wall and a second portion connected to the first longitudinal portion, the second portions of the interconnected hooks together forming a receiver adapted to receive the snare, each hook being formed of the material of the wall having the thickness, wherein the body includes an elongated spine connected to the pair of interconnected hooks as a single unitary structure, wherein the body comprises stent including a plurality of struts, the spine being wider in a circumferential direction than each of the plurality of struts.

* * * * *